(12) United States Patent
Baturin et al.

(10) Patent No.: US 9,724,063 B2
(45) Date of Patent: Aug. 8, 2017

(54) SURROGATE PHANTOM FOR DIFFERENTIAL PHASE CONTRAST IMAGING

(71) Applicant: Carestream Health, Inc., Rochester, NY (US)

(72) Inventors: Pavlo Baturin, Rochester, NY (US); Mark E. Shafer, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 213 days.

(21) Appl. No.: 14/517,072

(22) Filed: Oct. 17, 2014

(65) Prior Publication Data

US 2015/0110247 A1    Apr. 23, 2015

Related U.S. Application Data

(60) Provisional application No. 61/892,490, filed on Oct. 18, 2013.

(51) Int. Cl.
| | | |
|---|---|---|
| *G01N 23/00* | (2006.01) | |
| *A61B 6/00* | (2006.01) | |
| *A61B 6/03* | (2006.01) | |
| *G01N 23/20* | (2006.01) | |

(52) U.S. Cl.
CPC .............. *A61B 6/484* (2013.01); *A61B 6/482* (2013.01); *A61B 6/5205* (2013.01); *A61B 6/03* (2013.01); *A61B 6/583* (2013.01); *G01N 23/20075* (2013.01); *G01N 2223/3035* (2013.01)

(58) Field of Classification Search
CPC .. A61B 6/484; A61B 6/583; G01N 23/20075; G01N 2223/3035
See application file for complete search history.

(56) References Cited

U.S. PATENT DOCUMENTS

| | | | |
|---|---|---|---|
| 5,812,629 | A | 9/1998 | Clauser |
| 6,560,309 | B1 | 5/2003 | Becker et al. |
| 7,346,204 | B2 | 3/2008 | Ito |
| 7,453,981 | B2 | 11/2008 | Baumann et al. |
| 7,639,786 | B2 | 12/2009 | Baumann et al. |
| 7,646,843 | B2 | 1/2010 | Popescu et al. |

(Continued)

FOREIGN PATENT DOCUMENTS

| | | |
|---|---|---|
| DE | 102006015356 | 8/2007 |
| EP | 1 731 099 | 12/2006 |

(Continued)

OTHER PUBLICATIONS

International Search Report, International application No. PCT/US2014/066027, mailing date May 2, 2015, 2 pages.

(Continued)

*Primary Examiner* — Dani Fox

(57) ABSTRACT

A phantom material may be irradiated with varying energy x-rays to determine its phase shift properties. A determination of the difference between those phase shift properties and the phase shift properties of another material of interest can be represented and stored in terms of a polynomial function. The stored function can then be used in combination with a surrogate phantom shaped in the form of another object to obtain the phase shift properties of that other object as if it were made from the material of interest.

17 Claims, 5 Drawing Sheets

(56) References Cited

U.S. PATENT DOCUMENTS

| | | | |
|---|---|---|---|
| 7,693,256 | B2 | 4/2010 | Brahme et al. |
| 7,817,777 | B2 | 10/2010 | Baumann et al. |
| 8,515,002 | B2 | 8/2013 | Huang et al. |
| 8,855,395 | B2 | 10/2014 | Baturin et al. |
| 9,001,967 | B2 | 4/2015 | Baturin et al. |
| 9,357,975 | B2 | 6/2016 | Baturin et al. |
| 9,494,534 | B2 | 11/2016 | Baturin et al. |
| 2005/0249328 | A1 | 11/2005 | Bruder et al. |
| 2007/0183560 | A1 | 8/2007 | Popescu et al. |
| 2007/0183582 | A1 | 8/2007 | Baumann et al. |
| 2007/0183583 | A1 | 8/2007 | Baumann et al. |
| 2008/0014643 | A1 | 1/2008 | Bjorkholm |
| 2008/0123805 | A1 | 5/2008 | Zellerhoff |
| 2008/0273653 | A1 | 11/2008 | Niwa et al. |
| 2009/0092227 | A1 | 4/2009 | David et al. |
| 2009/0116720 | A1 | 5/2009 | Ritman |
| 2010/0220832 | A1 | 9/2010 | Ning et al. |
| 2010/0220834 | A1 | 9/2010 | Heismann et al. |
| 2010/0246764 | A1 | 9/2010 | Itoh et al. |
| 2010/0246765 | A1 | 9/2010 | Murakoshi et al. |
| 2010/0272235 | A1 | 10/2010 | Takahashi |
| 2011/0085639 | A1 | 4/2011 | Nakamura et al. |
| 2011/0135057 | A1 | 6/2011 | Mori et al. |
| 2011/0206181 | A1 | 8/2011 | Linev |
| 2011/0243305 | A1* | 10/2011 | Tada ............. A61B 6/4291 378/87 |
| 2012/0020461 | A1 | 1/2012 | Roessl et al. |
| 2012/0045108 | A1 | 2/2012 | Shechter |
| 2012/0057677 | A1 | 3/2012 | Vogtmeier et al. |
| 2012/0093284 | A1 | 4/2012 | Takemoto et al. |
| 2012/0114098 | A1 | 5/2012 | Mikami et al. |
| 2012/0163554 | A1 | 6/2012 | Tada |
| 2012/0250972 | A1 | 10/2012 | Tada et al. |
| 2013/0010926 | A1 | 1/2013 | Tada |
| 2013/0028378 | A1 | 1/2013 | Stutman et al. |
| 2013/0156284 | A1 | 6/2013 | Koehler et al. |
| 2013/0259194 | A1 | 10/2013 | Yip et al. |
| 2013/0308750 | A1 | 11/2013 | Ishii |
| 2014/0044234 | A1 | 2/2014 | Hashimoto et al. |
| 2014/0177789 | A1 | 6/2014 | Baturin et al. |
| 2014/0185746 | A1 | 7/2014 | Baturin et al. |
| 2014/0185896 | A1 | 7/2014 | Baturin et al. |
| 2014/0226782 | A1 | 8/2014 | Stutman et al. |
| 2014/0226783 | A1 | 8/2014 | Ning et al. |
| 2014/0226785 | A1 | 8/2014 | Stutman et al. |
| 2014/0270060 | A1 | 9/2014 | Date et al. |
| 2014/0270061 | A1 | 9/2014 | Yamaguchi |
| 2014/0341347 | A1 | 11/2014 | Radicke |
| 2014/0355740 | A1 | 12/2014 | Koehiler et al. |
| 2015/0092916 | A1 | 4/2015 | Baturin et al. |
| 2015/0110247 | A1 | 4/2015 | Baturin et al. |
| 2015/0117599 | A1 | 4/2015 | Yun et al. |
| 2015/0187096 | A1 | 7/2015 | Baturin et al. |
| 2015/0216499 | A1 | 8/2015 | Martens et al. |
| 2016/0038107 | A1 | 2/2016 | Baturin et al. |
| 2016/0095562 | A1 | 4/2016 | Baturin et al. |

FOREIGN PATENT DOCUMENTS

| | | |
|---|---|---|
| WO | 2011/122715 | 10/2011 |
| WO | 2012/029048 | 3/2012 |
| WO | 2012/080125 | 6/2012 |
| WO | 2013/126296 | 8/2013 |
| WO | 2014/137318 | 9/2014 |

OTHER PUBLICATIONS

International Search Report, International application No. PCT/US2014/066033, mailing date Apr. 28, 2015, 2 pages.

International Search Report, International application No. PCT/US2013/026301, mailing date Jun. 3, 2013, 3 pages.

International Search Report, International application No. PCT/US2013/075898, mailing date Apr. 22, 2014, 2 pages.

Supplementary European Search Report, dated Nov. 27, 2015, European Application No. 13769560.7, 2 pages.

International Search Report, mailed Feb. 2, 2017 for International Application No. PCT/US2016/062389, 2 pages.

Thomas Thuring, Compact X-ray grating interferometry for phase and dark-field computed tomography in the diagnostic energy range, Swiss Federal Institute of Technology Zurich, 2013, pp. 1-180.

Thomas Thuring, et al., Non-linear regularized phase retrieval for unidirectional X-ray differential phase contrast radiography, Optics Express, vol. 19, Issue 25, pp. 25545-25558, Optical Society of America 2011, issn: 10944087.

C. Kottler et al., Grating interferometer based scanning setup for hard x-ray phase contrast imaging, Review of Scientific Instruments, vol. 78, 034710, 2007, pp. 1-4.

H.N. Cardinal and A. Fenster "An accurate method for direct dual-energy calibration and decomposition" Medical Physics, May-Jun. 1990; vol. 17, No. 3, pp. 327-341.

Chapman, D., Thomlinson, et al., "Diffraction enhanced x-ray imaging," Phys. Med. Biol., 42, 2015, (1997).

Bonse, et al., "An x-ray interferometer," Appl. Phys. Lett. 6(8), 155-156, (1965).

Ingal. V. N., et al., "X-ray plane-wave topography observation of the phase contrast from non-crystalline object," J. Phys. D 28(11), 2314-2317, (1995).

Wilkins, S. W., et al., "Phase-contrast imaging using polychromatic hard X-rays," Nature (London) 384(6607) 335-338, (1996).

Momose, A., et al., "Demonstration of X-ray Talbot interferometry," Jpn. J. Appl. Phys. 42, L866-L868, (2003).

Wietkamp, T., et al., "X-ray phase imaging with a grating interferometer," Opt. Exp. 13(16), 6296-6304, (2006).

Pfeiffer, F., "Phase retrieval and differential phase-contrast imaging with low-brilliance X-ray sources", Nature Phys. 2, 258-261, (2006).

Fu, J. et al., "Helical differential X-ray phase-contrast computed tomography," Physica Medica, 30, 2014, pp. 374-379.

\* cited by examiner

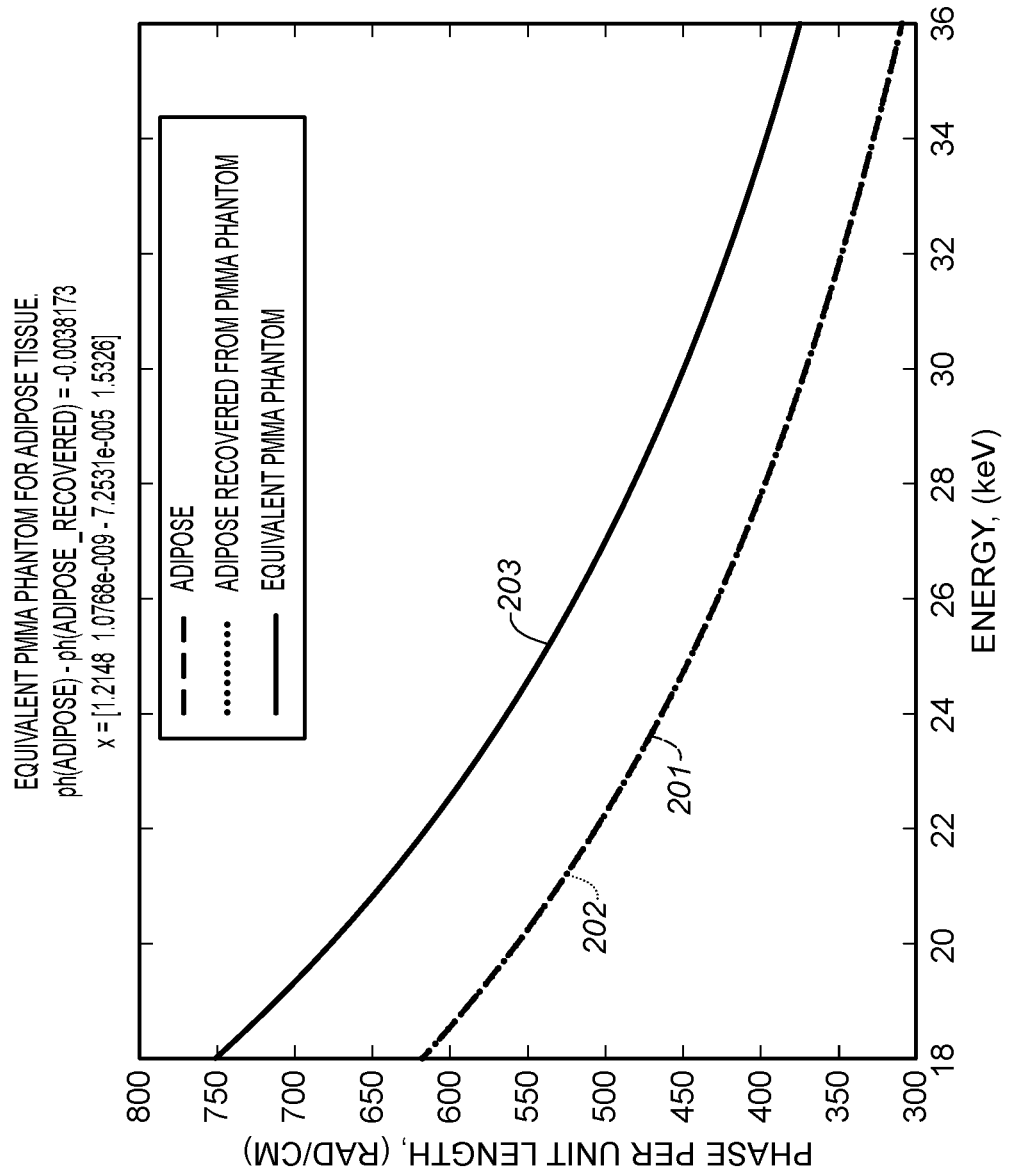

SURROGATE PHANTOM FOR DIFFERENTIAL PHASE CONTRAST IMAGING

CROSS REFERENCE TO RELATED APPLICATIONS

This application claims priority to U.S. Patent Application Ser. No. 61/892,490, filed Oct. 18, 2013, in the name of Baturin et al., and entitled SURROGATE PHANTOM FOR DIFFERENTIAL PHASE CONTRAST IMAGING.

This application is related in certain respects to U.S. Patent Application Ser. No. 61/939,925, filed Feb. 14, 2014, in the name of Baturin et al., and entitled METHOD AND APPARATUS FOR FABRICATION AND TUNING OF GRATING-BASED DIFFERENTIAL PHASE CONTRAST IMAGING SYSTEM; U.S. patent application Ser. No. 14/143,183, filed Dec. 30, 2013, in the name of Baturin et al., and entitled PHASE RETRIEVAL FROM DIFFERENTIAL PHASE CONTRAST IMAGING; U.S. patent application Ser. No. 14/499,762, filed Sep. 29, 2014, in the name of Baturin et al., and entitled MATERIAL DIFFERENTIATION WITH PHASE CONTRAST IMAGING; U.S. patent application Ser. No. 14/143,254, filed Dec. 30, 2013, in the name of Baturin et al., and entitled LARGE FOV PHASE CONTRAST IMAGING BASED ON DETUNED CONFIGURATION INCLUDING ACQUISITION AND RECONSTRUCTION TECHNIQUES; U.S. patent application Ser. No. 13/732,767, filed Jan. 2, 2013, in the name of Baturin et al., and entitled CONDITIONAL LIKELIHOOD MATERIAL DECOMPOSITION AND METHODS OF USING THE SAME; U.S. patent application Ser. No. 13/729,443, filed Dec. 28, 2012, in the name of Baturin et al., and entitled SPECTRAL GRATING-BASED DIFFERENTIAL PHASE CONTRAST SYSTEM FOR MEDICAL RADIOGRAPHIC IMAGING; U.S. patent application Ser. No. 13/724,096, filed Dec. 21, 2012, in the name of Baturin et al., and entitled GRATING-BASED DIFFERENTIAL PHASE CONTRAST IMAGING SYSTEM WITH ADJUSTABLE CAPTURE TECHNIQUE FOR MEDICAL RADIOGRAPHIC IMAGING; all seven of which are incorporated herein by reference in their entirety.

BACKGROUND OF THE INVENTION

The present invention is directed to a method and apparatus of creating a surrogate (or equivalent) phantom for differential phase contrast imaging. The surrogate phantom may be designed such that it mimics the phase shift properties of a material of interest, which for various reasons cannot be presented in the form of a phantom.

FIELD OF THE INVENTION

Conventional x-ray imaging devices take advantage of absorption information to probe the interior structures of objects. Many phantoms are built such that the absorption properties of the material of interest are mimicked as closely as possible at different x-ray beam or radiation conditions. With the development of phase contrast x-ray imaging technology, where the wave nature of x-rays is taken into account, it becomes important to characterize materials in terms of their wave propagation properties. In particular, the phase shift of x-ray beams passing through materials is of great importance. Knowing such a property can allow a better material separation or identification in a multi-material imaged object. Although the absorption properties can be satisfactory, wave propagation properties in an absorption phantom are not necessarily the same as the wave propagation properties would be in a real material sample. Therefore, there is a need to develop a phantom, which can mimic the wave propagation properties, especially for those materials which, for various reasons, cannot be used as a phantom material. For example, organic biological samples (such as breast tissue and others) are not suitable for long term preservation and cannot be easily handled (e.g., in contrast to inorganic phantoms). Thus, there may be a need to create a surrogate phantom to represent some organic material, such as human body tissue.

The discussion above is merely provided for general background information and is not intended to be used as an aid in determining the scope of the claimed subject matter.

BRIEF DESCRIPTION OF THE INVENTION

Certain exemplary embodiments disclosed herein may be used to create or provide a surrogate phantom (e.g., polymethyl methacrylate (PMMA) phantom) to represent some organic material (e.g., breast tissue). Certain exemplary embodiments disclosed herein may be used to define a framework of phantom formation having desired phase shift material properties and/or disclose areas of phantom application.

In one embodiment, a method comprises irradiating with x-rays a phantom material having a volume formed into a preselected shape. A phase shift in the x-rays that have passed through the volume of phantom material is measured, and a polynomial is determined that represents a difference between the measured phase shift and a phase shift of a material of interest. The measured phase shift is modified using the determined polynomial to obtain the phase shift of the material of interest.

In another embodiment, a computer implemented method comprises storing phase shift data of a first material, storing phase shift data of a sample mammalian soft tissue, determining a plurality of polynomial coefficients of a polynomial function that represents a difference between the phase shift data of the first material and the phase shift data of the mammalian soft tissue. Thereafter, the plurality of polynomial coefficients is stored as well as the polynomial function. Phase shift data of a phantom made from the first material and shaped in the form of the mammalian soft tissue is determined and stored. The polynomial function and the plurality of coefficients can then be used to determine phase shift data of the mammalian soft tissue.

These, and other, aspects and objects of the present invention will be better appreciated and understood when considered in conjunction with the following description and the accompanying drawings. It should be understood, however, that the following description, while indicating preferred embodiments of the present invention and numerous specific details thereof, is given by way of illustration and not of limitation. For example, the summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The figures below are intended to be drawn neither to any precise scale nor with respect to relative size, angular relationship, or relative position nor to any combinational relationship with respect to interchangeability, substitution, or representation of an actual implementation.

BRIEF DESCRIPTION OF THE DRAWINGS

So that the manner in which the features of the invention may be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments, emphasis generally being placed upon illustrating the features of certain embodiments of the invention. In the drawings, like numerals are used to indicate like parts throughout the various views. Thus, for further understanding of the invention, reference may be made to the following detailed description, read in connection with the drawings in which:

FIG. 2A is a plot of a PMMA surrogate phantom for adipose tissue;

DETAILED DESCRIPTION OF THE INVENTION

Figure 1B:
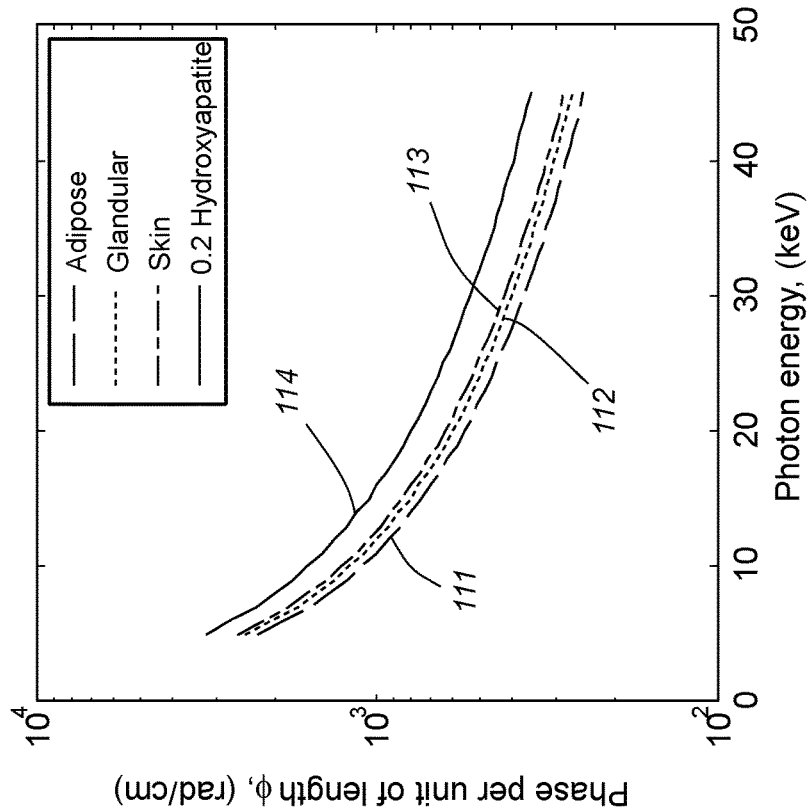
FIGS. 1A-B are plots showing the linear attenuation and phase shift per unit of length (1/cm) for adipose, glandular, skin, and 20% mixture of hydroxyapatite.

Conventional medical diagnostic x-ray imaging devices rely on absorption properties of materials to provide information about the interior structure of imaged objects. Such absorption type of imaging assumes non-refractive x-rays penetrating the object being imaged. The image contrast is produced due to the differences in the absorption cross section. While generally good contrast between highly attenuating (hard) and weakly attenuating (soft) materials is observed, the differentiation between soft-tissue materials can be difficult due to a low relative contrast. For example, the low-contrast soft tissue materials including, but not limited to, vessels, cartilages, lungs, and breast tissues provide poor contrast in comparison to highly attenuating structures such as bone. The problem of soft-tissue imaging may be addressed by interferometric x-ray imaging devices, which take advantage of the wave nature of x-ray radiation. One example of an interferometric imaging device is a differential phase contrast based imager. Such imaging interferometers focus on measuring the refraction characteristics manifested in the process of x-rays passing through the object of study. In addition to absorption images these devices can provide differential phase contrast images and dark field images.

In recent years, interferometric x-ray imaging devices have been used to address the problem of low contrast in soft tissue imaging. In addition to conventional absorption, such devices take advantage of the wave nature of x-ray radiation to measure a phase change in the radiation caused by diffraction of x-rays penetrating the imaged object. When an x-ray, as an electromagnetic wave, penetrates a material medium, its amplitude is attenuated and its phase is shifted. The material dependent index of refraction can be represented as $$n = 1 - \delta + i\beta, \quad (1)$$

where the imaginary part $\beta$ contributes to the attenuation of the amplitude and the real part $\delta$ (refraction index decrement) is responsible for the phase shift. While the interferometer type of imaging devices can measure both $\beta$ and $\delta$ terms, the conventional x-ray imaging devices can detect only $\beta$, which is the absorption, or attenuation, term. It is known that $\beta$ and $\delta$ are proportional to atomic scattering factors of the material. For example, for a compound of density $\rho$ the refractive index, shown in equation (1), can be expressed in terms of the compound's atomic scattering factors $f_1$ and $f_2$ as:

$$n \cong 1 - \frac{r_e N_a \lambda^2 \rho}{2\pi} \left( \sum_k x_k (f_{1,k} + i f_{2,k}) \right) \Big/ \left( \sum_k x_k A_k \right) \quad (2)$$

where $r_e$, $N_a$, $\lambda$, and $\rho$ are, respectively, the electron radius, Avogadro number, photon wavelength, and effective density of the compound, or material. The summation is taken over the relative concentrations $x_k$ of each of the chemical elements of atomic mass $A_k$ making up the compound. Using equation (2) it can be shown that the real part $\delta$ (in units of rad/cm) is about $10^3$ to $10^4$ times larger than the imaginary part $\beta$ (in units of 1/cm). This provides a potential for imaging soft-tissue materials with higher contrast. When the x-ray is passing through a bodily tissue or other object, its attenuation and phase shift can be calculated as:

$$\begin{cases} \mu(x, y) = \frac{4\pi}{\lambda} \int \beta(x, y, z) dz \\ \varphi(x, y) = \frac{2\pi}{\lambda} \int \delta(x, y, z) dz \end{cases} \quad (3)$$

Figure 1A:
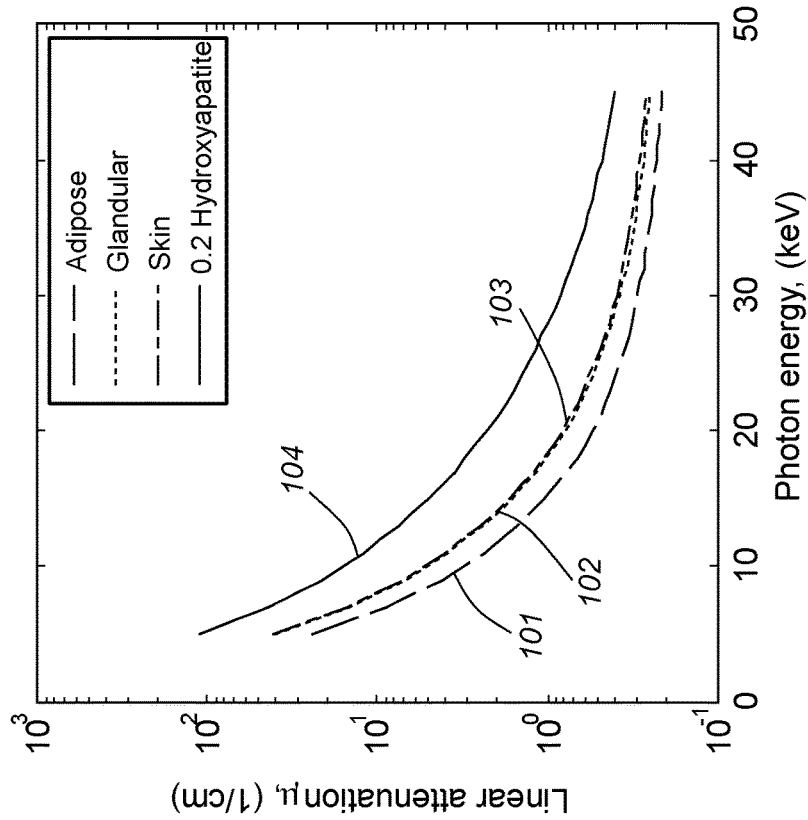

Using equations (1)-(3), it is possible to model absorption and phase shift properties of any material of known density and/or known elemental composition (e.g., chemical formula or weight fractions of individual elemental components). For example, FIG. 1A shows the attenuation and FIG. 1B shows phase shift per unit of length over a range of x-ray energies for materials that are known, and can be common, for a breast: adipose tissue 101, 111; glandular tissue 102, 112; skin 103, 113; and 20% hydroxyapatite water-based mixture 104, 114, which can represent, e.g., a calcification.

For the most part, biological tissues do not exhibit energy curve discontinuities in some radiographic diagnostic energy ranges (e.g., 10-50 keV). As we observe in FIGS. 1A-B, the curves have polynomial dependence on energy and are shifted, or scaled (for example, vertically), with respect to each other. Using these observations, we can represent the phase shift of an x-ray wave through a phantom as:

$$\phi_{Phantom}(E) = x_1 \cdot \phi_{Material}(E) + (x_2 \cdot E^2 + x_3 \cdot E + x_4) \quad (4)$$

Here, $x_1$ represents the scaling factor, which provides a vertical shift (or scaling) of the phantom energy curve, and the second order polynomial term in parenthesis is used to reshape the phantom energy curve such that it matches the energy dependence curve of a material of interest, i.e., the equation (4) may be used to mimic the energy dependence curve (phase shift) of the material of interest based on the response data of the phantom. Higher order polynomials can also be used/added if desired, or if necessary, for greater accuracy. According to equation (4), one needs to define parameters $x_1$, $x_2$, $x_3$, and $x_4$ to express the phase shift of the phantom in terms of the actual phase shift of the material of interest. Thereafter, the parameters can be stored and subsequently applied in equation (4) to mimic the energy dependence curve of the material of interest.

In one embodiment, such parameters can be found using a minimization technique. For example, a least squares minimization, as follows:

$$\min\left(\sum_i [\varphi_{Phantom}(E) - (x_1 \cdot \varphi_{Material}(E) + x_2 \cdot E^2 + x_3 \cdot E + x_4)]^2\right) \quad (5)$$

Figure 2B:
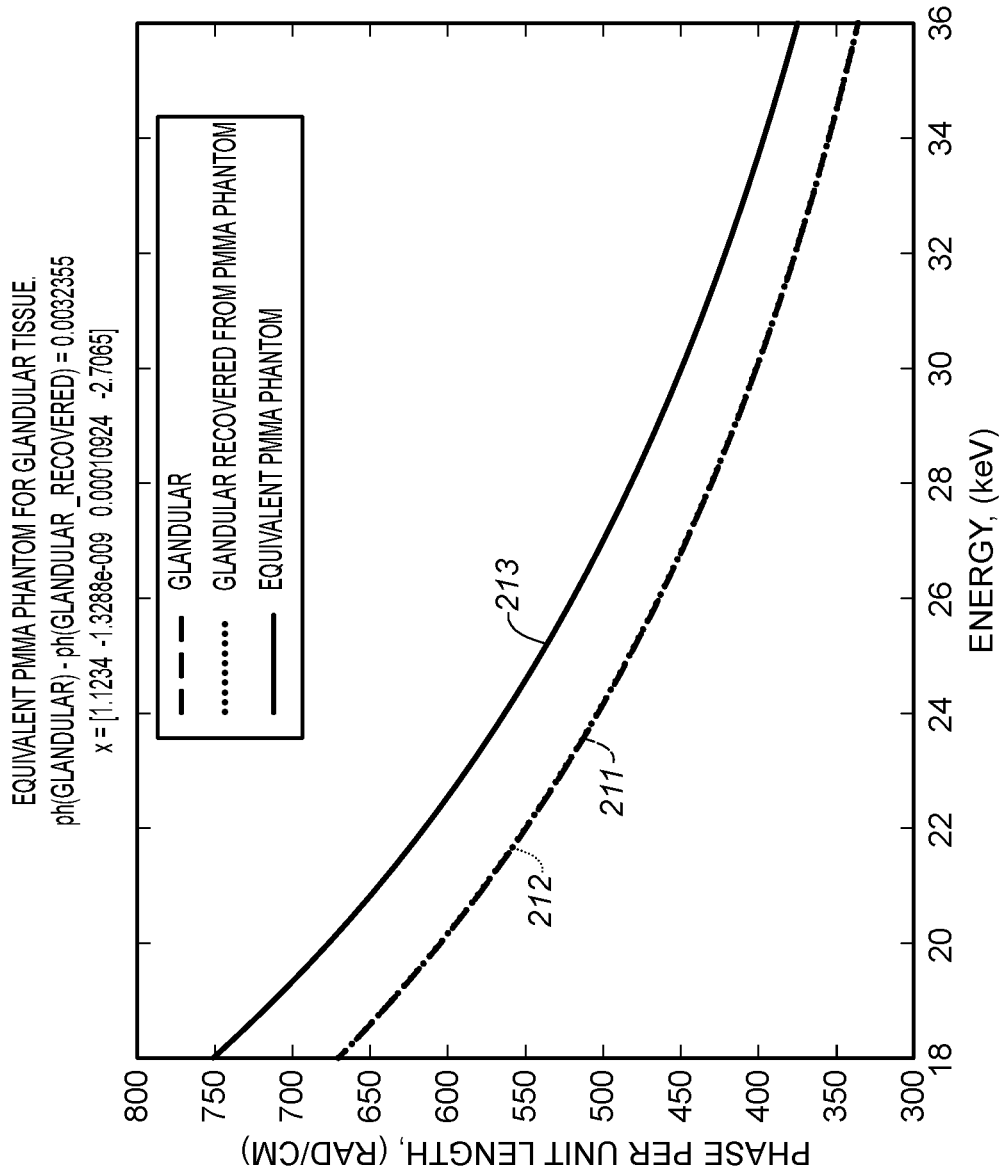
FIG. 2B is a plot of a PMMA surrogate phantom for glandular tissue.
Figure 2C:
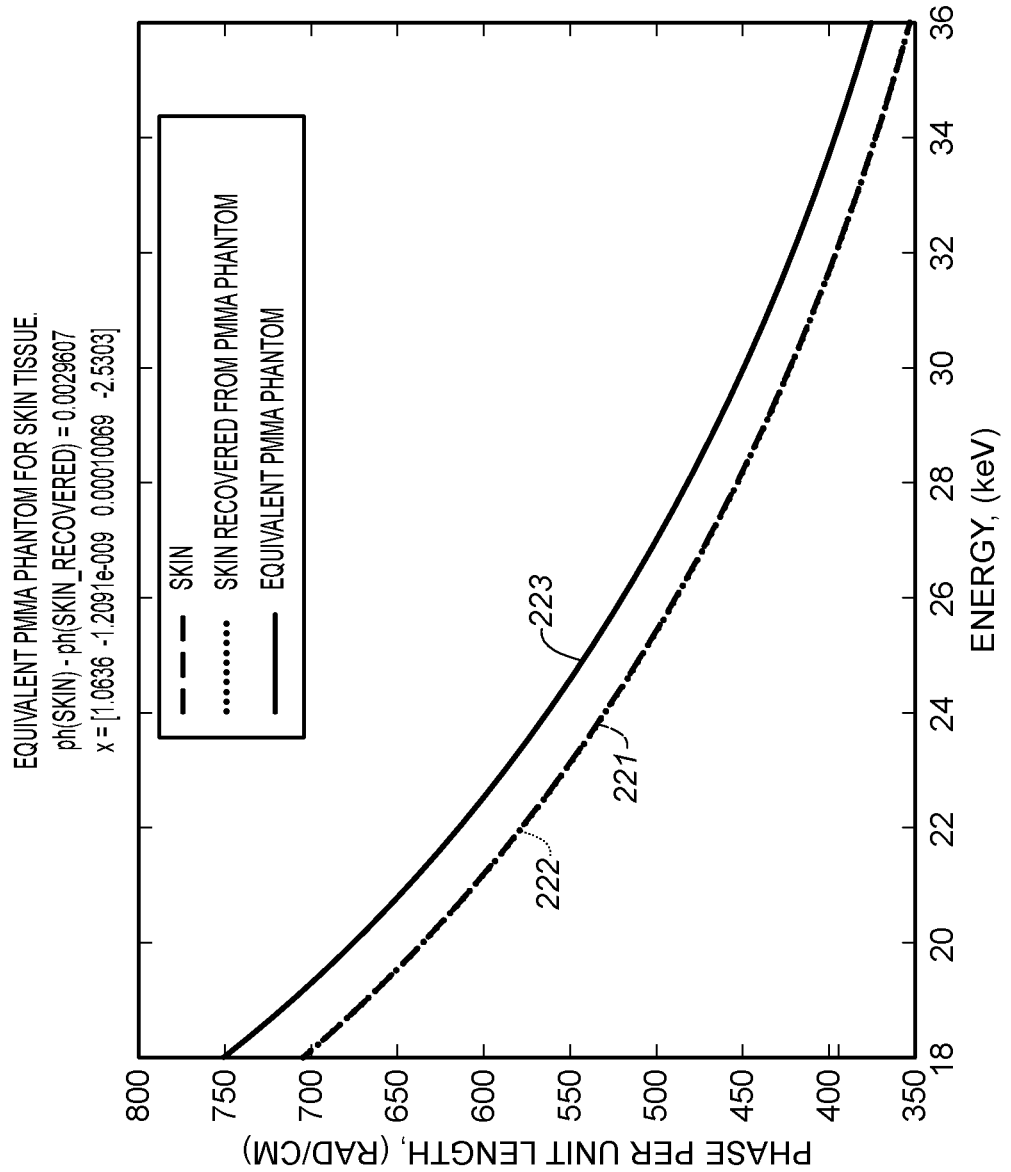
FIG. 2C is a plot of a PMMA surrogate phantom for skin tissue.

Alternatively, other minimization techniques can be used. As an example, with respect to FIGS. 2A-2C, there are illustrated energy dependence curves for poly-methyl methacrylate (PMMA) phantoms, which can serve as a substitute for adipose tissue as shown in FIG. 2A; for glandular tissue as shown in FIG. 2B; or for skin tissue as shown in FIG. 2C. With respect to FIG. 2A, the PMMA phantom energy dependence curve 203 is shown together with the adipose energy dependence curve 201, and the energy dependence curve of adipose tissue as calculated 202, or recovered, based on the PMMA phantom using the equation (4). The parameter values are as follows: $x_1$=1.2148; $x_2$=1.0768×10$^{-9}$; $x_3$=−7.2531×10$^{-5}$; and $x_4$=1.5326. With respect to FIG. 2B, the PMMA phantom energy dependence curve 213 is shown together with the glandular energy dependence curve 211, and the energy dependence curve of glandular tissue as calculated 212, or recovered, based on the PMMA phantom using the equation (4). The parameter values are as follows: $x_1$=1.1234; $x_2$=−1.3288×10$^{-9}$; $x_3$=1.0924×10$^{-4}$; and $x_4$=−2.7065. With respect to FIG. 2C, the PMMA phantom energy dependence curve 223 is shown together with the skin energy dependence curve 221, and the energy dependence curve of skin tissue as calculated 222, or recovered, based on the PMMA phantom using the equation (4). The parameter values are as follows: $x_1$=1.0636; $x_2$=−1.2091×10$^{-9}$; $x_3$=1.0069×10$^{-4}$; and $x_4$=−2.5303. The parameter $x_1$ is unitless, while the units of the rest of parameters $x_2$, $x_3$, and $x_4$ are, respectively, $$\frac{rad}{cm}\frac{1}{eV^2}, \frac{rad}{cm}\frac{1}{eV}, \text{ and } \frac{rad}{cm}.$$

With respect to the FIGS. 2A-2C, the PMMA curves 203, 213, 223, and the material curves 201 (adipose), 211 (glandular), and 221 (skin) were simulated using equations (1)-(3). The calculated curves 202 (adipose), 212 (glandular), and 222 (skin) show the material dependence calculated from equation (4), i.e., solved for $\varphi_{Material}(E)$. These calculated curves 202, 212, 222, may be displayed with the simulated curves 201, 211, 221, to check the quality of the fit. As exemplified in FIGS. 2A-2C, the same PMMA phantom material can be used to represent a plurality of the known tissues, but not limited to these, by using the corresponding fit parameters $x_1$, $x_2$, $x_3$, and $x_4$. Such fit parameters may be determined for a variety of materials and reused.

Figure 3:
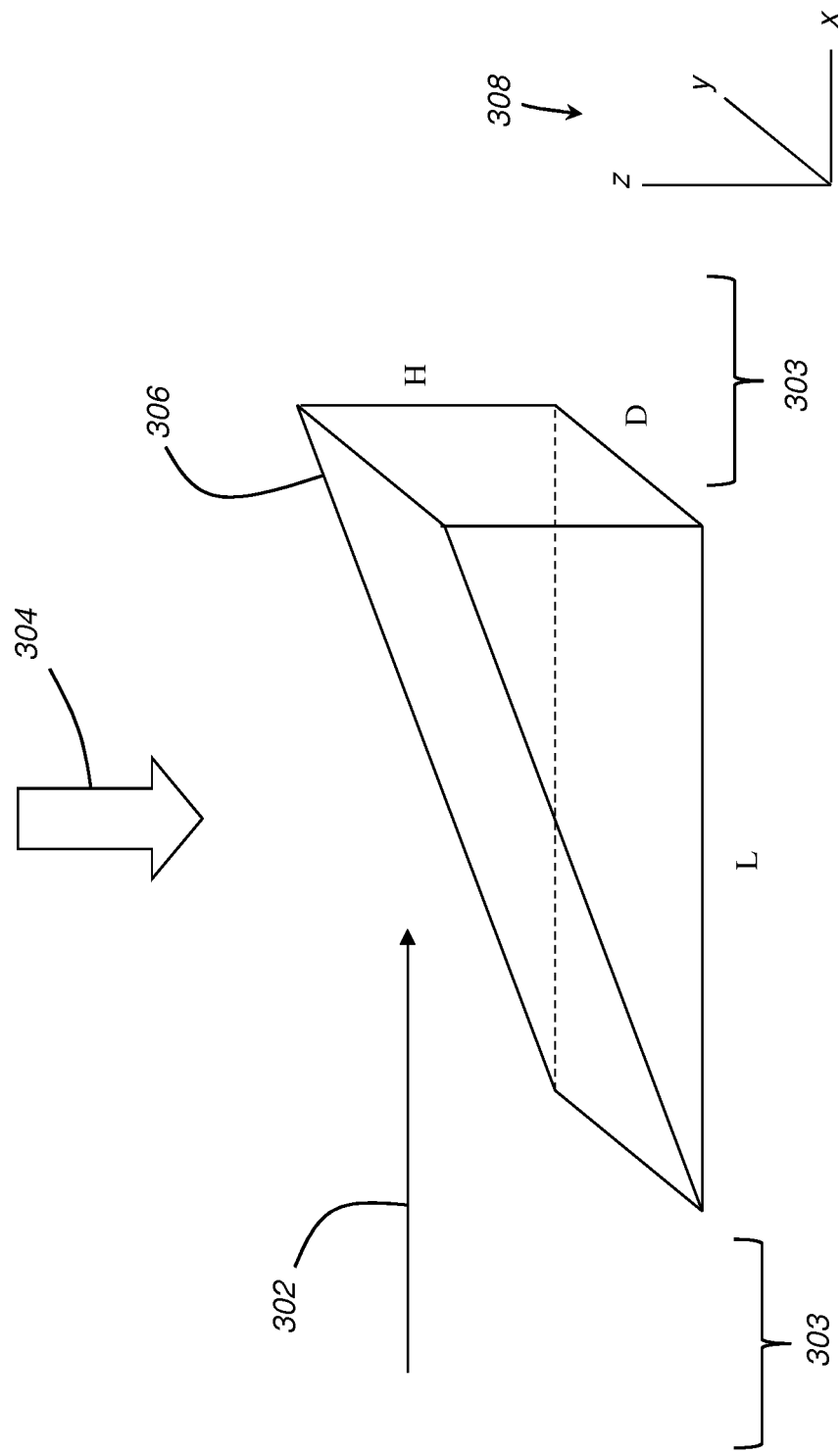
FIG. 3 is an example of a wedge phantom for measuring phase shift properties.

Certain exemplary embodiments according to the present application can be used to determine the energy dependence of material phase shift experimentally. An example of a phantom according to the present application, which can be used to extract the material phase shift, is shown in FIG. 3. Note that any other phantom shape, for example, a step phantom, which can allow phase shift measurements, may also be used. Also, a wedge, a stepped wedge, cylindrical, conical, frustoconical, cubic, rectangular solid, plate, disk, spherical, or other regular or irregular polyhedra and ellipsoids may be used. Alternatively, a container having a fill material may be used, wherein the fill material may include a gel, plasma, oil, water, or other liquid, fluid, or other semi-solid material. In the case of a biological tissue, one can measure a biopsy or a cadaver sample. Such energy dependencies can be determined, for example, by using measurements with monochromatic x-ray exposures. Alternatively, full spectrum x-ray exposures can be used in conjunction with an energy-resolving photon-counting detector. In the case of the energy-resolving photon-counting detector, the energy thresholds can be set such that a scan across the range of different energies can be performed similar to monochromatic exposures, i.e., using narrow energy thresholds. In one embodiment, when polychromatic x-ray exposures are used, the transmission can be expressed as:

$$T = \frac{\int_E S(E)R(E)\exp\left(-\int \mu(E,r)dr\right)dE}{\int_E S(E)R(E)dE} \quad (6)$$

where S(E) is the quanta distribution of the x-ray spectrum, R(E) is the spectral responsivity of the detector, and $\mu$(E) is the spectral attenuation of the object. Typically, the equation (6) can be rewritten in terms of system weighting factor W(E):

$$T = \int_E W(E)\exp\left(-\int \mu(E,r)dr\right)dE \quad (7)$$

where $$W(E) = \frac{S(E)R(E)}{\int_E S(E)R(E)dE}.$$

The spectral response function, R(E), is primarily a detector property and it can be modeled or found experimentally. The spectral distribution of the quanta, S(E), which, in a similar way, can be either modeled or measured, is a property of the x-ray source. It depends on properties of the x-ray source such as anode material, cathode voltage, and inherent and/or additional filtrations used during image acquisition. In one embodiment, when a surrogate phantom is scanned with known spectral quanta distribution and the detector's response function is known, the mean energy of the weighting factor can be used in equation (4) to make single-point measurement translations to a material of interest.

In terms of an application, exemplary surrogate phantom embodiments according to the present application would be practical for computed tomography type of phase contract imaging, where the reconstruction can result in attenuation and phase shift per unit of length. In one exemplary embodiment, a composite phantom that consists of several materials, with one of them being a surrogate material, can be scanned and then scaled using appropriate parameters in equation (4). In other embodiments, thresholded by means of different statistical approaches or other methods, background (or other materials) can be scaled back to initial values by using the same set of parameters from equation (4). Having surrogate material represented as material of interest and background, made of some other material and represented in its true, i.e., not scaled, values could also be useful for signal to noise estimates.

If the wedge phantom 306 illustrated in FIG. 3 is scanned from left to right as indicated by the arrow 302, the differential phase will be zero in the areas where the phantom is not present 303 and will be constant $$\left(\frac{\partial \varphi}{\partial x_W}\right)$$

in the area of the wedge 306 itself, since the phase change will be the same when moving across the wedge. The x-ray detector will measure the wedge in terms of pixels. Therefore, in one embodiment, it can be convenient estimating phase shift in units of radians per pixel. If x-rays 304 are incident perpendicular to the base of the wedge, i.e., x-rays 304 are parallel to the z-axis while the base is in the xy plane, as shown in the coordinates 308, then the phase shift per pixel (in the direction of the x-rays 304) is equal to $$\frac{L}{H}\frac{\partial \varphi}{\partial x_W}.$$

Alternatively, the phase shift per pixel can be extracted from the integrated phase image, represented by $$\varphi(x, y) = \int \frac{\partial \varphi}{\partial x} dx.$$

A linear fit of the integrated phase in the area of wedge will result in the wedge material's phase shift per pixel. Thus, to obtain energy dependence curves similar to those shown in FIGS. 2A-2C, the wedge phantom may be scanned at different mean energies. Similar scans should be conducted for materials of interest, such as a biological sample.

In one embodiment, to model the absorption properties of the material of interest, the same "matching" (or calibration) procedure can be done for absorption images of a surrogate phantom and material of interest. In other words, similar to equation (4), the relationship between surrogate phantom and material of interest should be established by fitting the linear attenuation curves, which would represent the absorption properties. This would allow obtaining corresponding x parameters, which can be used to scale the absorption image of the surrogate phantom back to an image of the material of interest.

The present application contemplates methods and program products recordable on any computer readable media for accomplishing the disclosed operations. Exemplary embodiments according to the present application may be implemented using an existing computer processor, or by a special purpose computer processor incorporated for this purpose. Also known in the art are digital radiographic imaging panels that utilize an array of pixels comprising an X-ray absorbing photoconductor, such as amorphous Selenium (a-Se), and a readout circuit. Since the X-rays are absorbed in the photoconductor, a separate scintillating screen is not required. It should be noted that while the present description and examples are primarily directed to radiographic medical imaging of a human or other subject, embodiments of the apparatus and methods of the present application can also be applied to other radiographic imaging applications. This includes applications such as non-destructive testing (NDT), for which radiographic images may be obtained and provided with different processing treatments in order to accentuate different features of the imaged subject.

As will be appreciated by one skilled in the art, the present invention may be embodied as a system, method, or computer program product. Accordingly, an embodiment of the present invention may be in the form of an entirely hardware embodiment, an entirely software embodiment (including firmware, resident software, micro-code, and other suitable encodings) or an embodiment combining software and hardware aspects that may all generally be referred to herein as a "circuit" or "system." Furthermore, the present invention may take the form of a computer program product embodied in a computer-readable storage medium, with instructions executed by one or more computers or processors. This medium may comprise, for example: magnetic storage media such as a magnetic disk (such as a hard drive or a floppy disk) or magnetic tape; optical storage media such as an optical disc, optical tape, or machine readable bar code; solid state electronic storage devices such as solid state hard drives, random access memory (RAM), or read only memory (ROM); or any other physical device or medium employed to store a computer program. The computer program for performing the method of the present invention may also be stored on computer readable storage medium that is connected to a host processor by way of the internet or other communication medium. Those skilled in the art will readily recognize that the equivalent of such a computer program product may also be constructed in hardware. In the context of this document, a computer-usable or computer-readable medium may be any medium that can contain, store, communicate, propagate, or transport computer instructions for use by, or in connection with, an instruction execution system, apparatus, or device.

Exemplary embodiments described herein may relate to methods and/or systems of operating a digital x-ray detector for the purpose of determining phase shift properties of a phantom and other objects. Exemplary embodiments described herein may relate to methods and/or systems of operating a digital x-ray detector using continuous read out of the imaging panel. Exemplary embodiments described herein may relate to methods and/or systems of operating a digital x-ray detector using multi-sample (e.g., two) continuous read out of the imaging panel (e.g., row by row).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method comprising:
irradiating with x-rays a phantom material having a volume formed into a preselected shape;
measuring a phase shift in the x-rays that have passed through the volume of phantom material; and
modifying the measured phase shift in the x-rays using a predetermined polynomial to obtain a phase shift of a material of interest.

2. The method of claim 1, further comprising determining a polynomial that represents a difference between the measured phase shift in the x-rays and the phase shift of the material of interest to obtain the predetermined polynomial.

3. The method of claim 1, wherein a composition of the volume of phantom material is known substantially in its entirety.

4. The method of claim 1, wherein the composition of the volume of phantom material is homogeneous.

5. The method of claim 1, wherein the volume of phantom material is non-homogeneous and comprises a plurality of known compounds.

6. The method of claim 1, wherein the preselected shape of the volume of phantom material is selected from the group consisting of a wedge, a stepped wedge, cylindrical, conical, frustoconical, cubic, rectangular solid, plate, disk, spherical, or other regular or irregular polyhedra and ellipsoids.

7. The method of claim 1, wherein the preselected shape of the volume of phantom material comprises a hollow container having a gel, plasma, oil, water, liquid, fluid, or other solid or semi-solid material therein.

8. The method of claim 1, wherein the step of irradiating comprises repeatedly irradiating the phantom material each time using x-rays having a different energy level.

9. The method of claim 1, wherein the material of interest is human body tissue.

10. The method of claim 1, further comprising storing the polynomial in an electronic memory that is capable of being accessed by a computer system for subsequent calculations of a phase shift of another object made from the material of interest.

11. The method of claim 10, further comprising storing the polynomial in an electronic memory that is capable of being accessed by a computer system for subsequent calculations of a phase shift of a volume of the phantom material having a different preselected shape.

12. The method of claim 11, further comprising storing the polynomial in an electronic memory that is capable of being accessed by a computer system for subsequent calculations of a phase shift of said another object made from the material of interest and having said different preselected shape.

13. The method of claim 10, wherein the stored polynomial comprises four coefficients representing the difference between the measured phase shift and the phase shift of the material of interest.

14. The method of claim 1, wherein the step of measuring comprises measuring a phase shift per unit of length of the volume of phantom material.

15. The method of claim 1, wherein the material of interest is selected from the group consisting of glandular tissue, adipose tissue, and skin tissue.

16. The method of claim 1, wherein the phase shift of the material of interest is determined by a simulation.

17. The method of claim 1, wherein the phase shift of the material of interest is determined by an actual phase shift measurement of the material of interest.

* * * * *